United States Patent [19]
Sunalp

[11] Patent Number: 5,433,190
[45] Date of Patent: Jul. 18, 1995

[54] EYELID SPECULUM DEVICE

[76] Inventor: Murad A. Sunalp, 6095 N. Bungalow La., Fresno, Calif. 93704

[21] Appl. No.: 110,099

[22] Filed: Aug. 20, 1993

[51] Int. Cl.$^6$ .............................................. A61F 9/007
[52] U.S. Cl. ..................................... 600/236; 606/107
[58] Field of Search ................. 128/20, 17, 18, 12, 128/13; 606/107, 166, 198; 604/294, 295, 302

[56] References Cited

U.S. PATENT DOCUMENTS

| | | |
|---|---|---|
| 1,389,436 | 8/1921 | Cameron . |
| 2,238,563 | 4/1941 | Jacques . |
| 2,438,646 | 3/1948 | Pulliam .............................. 128/20 |
| 2,702,540 | 2/1955 | Debeh ............................... 128/20 |
| 3,054,398 | 9/1962 | Kobler .............................. 128/20 |
| 3,241,550 | 3/1966 | Gelarie . |
| 3,841,318 | 10/1974 | Olson . |
| 4,023,560 | 5/1977 | Cade et al. . |
| 4,037,589 | 7/1977 | McReynolds ....................... 128/20 |
| 4,200,089 | 4/1980 | Inoue ................................. 128/12 |
| 4,321,916 | 3/1982 | McKee . |
| 4,782,820 | 11/1988 | Woods . |
| 5,064,420 | 11/1991 | Clarke et al. . |
| 5,070,860 | 12/1991 | Grounauer . |
| 5,164,519 | 11/1992 | Goldman . |

OTHER PUBLICATIONS

Advertisement of Bristol-Myers Squibb Company, Jacksonville, Fla., for a Lid-Set Surgical Eyelid Retractor, Dated Nov., 1992.

*Primary Examiner*—Richard J. Apley
*Assistant Examiner*—Donna L. Maraglio
*Attorney, Agent, or Firm*—Poms, Smith, Lande & Rose

[57] ABSTRACT

An eyelid speculum device used to hold a person's eyelids open for ocular surgery, treatment, examination, or some other reason. The device has two elongated arms, each arm having one free end. The other ends of the arms are attached to a joining member. A person may grasp gripping portions at the free ends of the arms, and move the arms toward each other until the gripping portions contact one another. The device may then be inserted between the upper and lower eyelids of a person's eye. The elongated arms engage the eyelids after the gripping portions are released. A substantial length of each arm engages the eyelids, because the arms are contoured to generally conform to the curvature and/or length of the eyelids. As a result, reduced pressure is applied to the eyelids, which decreases the chances that post-operative ptosis or drooping of the eyelids will occur.

16 Claims, 1 Drawing Sheet

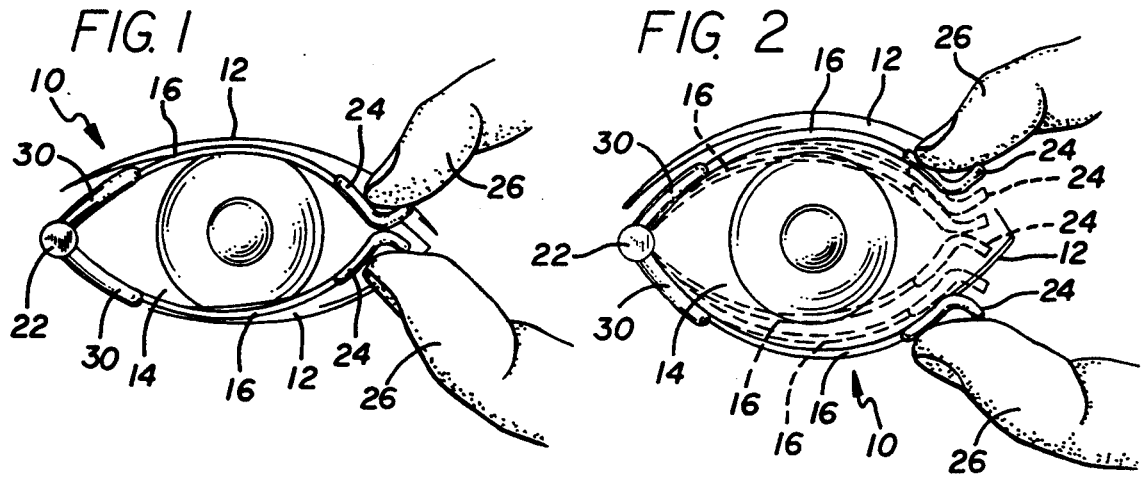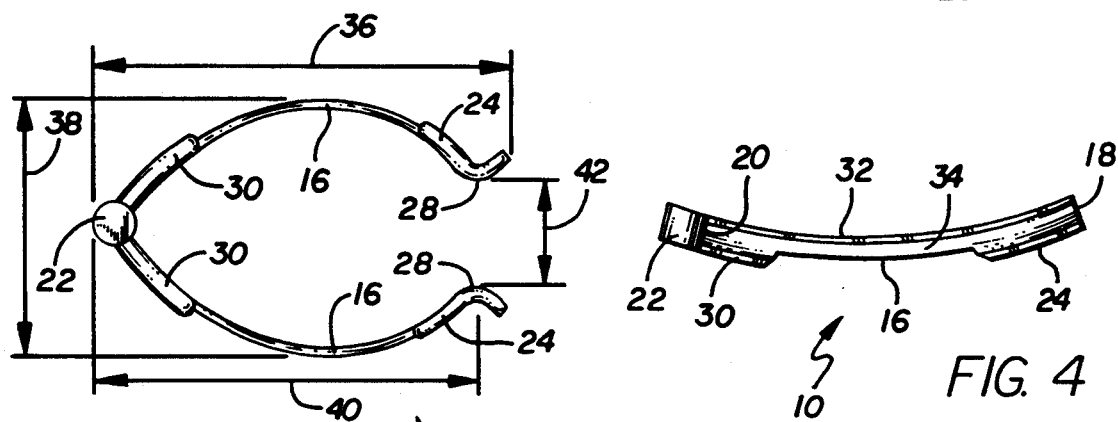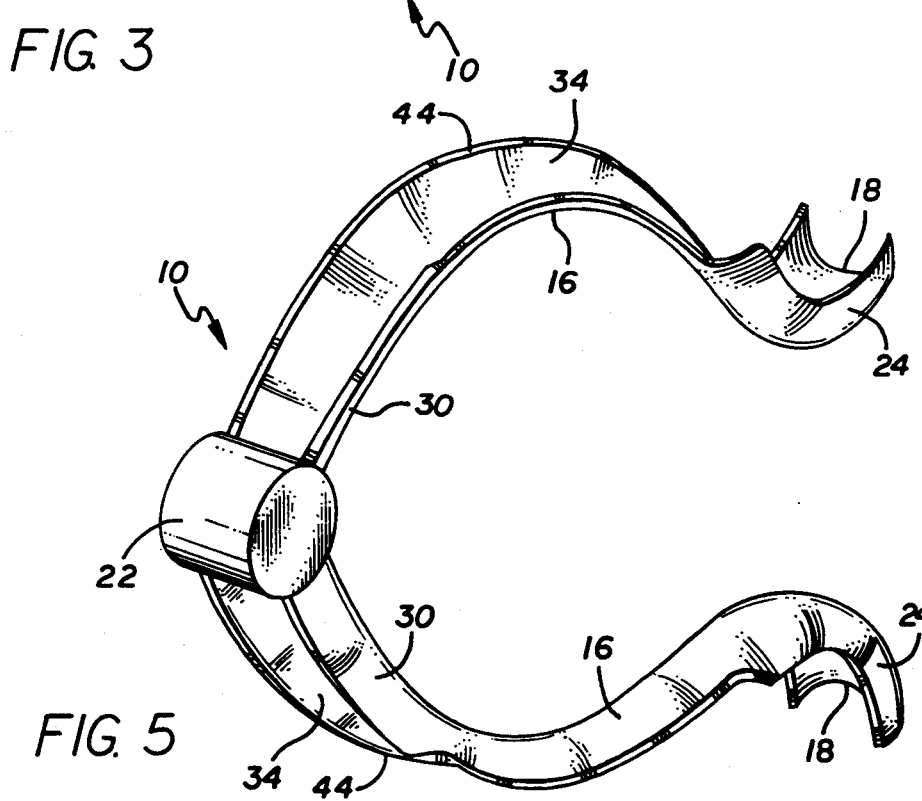

EYELID SPECULUM DEVICE

BACKGROUND OF THE INVENTION

The present invention relates generally to retractors or speculum devices, and more particularly to eyelid speculum devices used to hold a person's eyelids open.

In the past, different devices have been used for the purpose of holding a person's eyelids open to allow access to an eyeball for examination, treatment, ocular surgery, etc. For example, U.S. Pat. No. 5,070,860, issued to Grounauer on Dec. 10, 1991, discloses a retractor device used to retract a patient's eyelids. The device has two arms, each having one end thereof connected to a housing containing a spring used to bias or hold the arms apart. Spoons are connected to the other ends of the arms by elongated members hinged to the arms. The spoons engage the eyelids, holding the eyelids open. Strips of adhesive are attached to the spoons, and may be attached to a person's face for the purposes of keeping the spoons away from the eyeball, and providing stability for the device. The device also includes a ball-and-socket joint, and a base or foot covered by a double face adhesive, which is used to support the device on the temple of a person.

The above-described retractor device is expensive to manufacture, and difficult to mount on a patient's temple. Also, the size of the device makes it difficult to use. In addition, the spoons may apply excessive pressure to the eyelid muscles.

An eyelid retractor is described in U.S. Pat. No. 4,321,916, issued to McKee on Mar. 30, 1982. The retractor is formed from a loop of material such as wire, and includes a bridge portion, handle portion, and blade portions. The wire used for the device is sufficiently malleable to allow the bridge and handle portions to be bent so that the device will "hug" or rest on a patient's face. The blade portions engage the eyelids of a person's eyes, holding the lids open for surgery, examination, etc. The handle portions may be pinched or urged together so that the blade portions slip or pass under the eyelids. However, the wire retractor is relatively large, and blade portions of the retractor may apply excessive pressure to a person's eyelids. Also, it may be difficult to bend the handle portions of the retractor to fit the faces of different patients.

Other speculum or retractor devices are described in U.S. Pat. Nos. 5,163,419, issued to Goldman on Nov. 17, 1992 (device for expanding the pupil of an eye); 5,064,420, issued to Clarke, et al. on Nov. 12, 1991 (eyelid opener used with ophthalmic bottle containing fluid); 4,782,820, issued to Woods on Nov. 8, 1988 (iris retaining device for placement in pupillary opening of eye); 4,023,560, issued to Cade et al. on May 17, 1977 (female urinary device); 3,841,318, issued to Olson on Oct. 15, 1974 (vaginal speculum); 3,241,550, issued to Gelarie on Mar. 22, 1966 (mouth retractor); 2,238,562, issued to Jacques on Apr. 15, 1941 (embalming instrument used to hold an incision open); and 1,389,436, issued to Cameron on Aug. 30, 1921 (mouth retractor).

SUMMARY OF THE INVENTION

It is an object of this invention to provide an eyelid speculum device which may be used to hold a person's eyelids open for surgery, treatment, examination, or some other purpose.

It is another object of this invention to provide an eyelid speculum device which may be easily positioned between a person's eyelids and held in place without the use of adhesive tape or other supporting devices.

It is still another object of this invention to provide an eyelid speculum device which more uniformly applies pressure over a person's eyelids in order to prevent post-operative ptosis or dropping of the eyelids.

It is still another object of this invention to provide an eyelid speculum device which generally conforms to the shape of a person's eye, and is relatively simple in construction, and compact in size.

It is still another object of this invention to provide an eyelid speculum device which is economical to manufacture.

These and other objects and advantages are attained by an eyelid speculum device used to hold a person's eyelids open for ocular surgery, treatment, examination, or some other reason. The device has two elongated arms, each arm having one free end. The other ends of the arms are attached to a joining member. A person may grasp gripping portions at the free ends of the arms, and move the arms toward each other until the gripping portions contact one another. The device may then be inserted between the upper and lower eyelids of a person's eye. The elongated arms engage the eyelids after the gripping portions are released. A substantial length of each arm engages the eyelids, because the arms are contoured to generally conform to the curvature and/or length of the eyelids. As a result, reduced pressure is applied to the eyelids, which decreases the chance that post-operative ptosis or drooping of the eyelids will occur.

The various features of the present invention will be best understood together with further objects and advantages by reference to the following description of the preferred embodiment taken in conjunction with the accompanying drawings.

BRIEF DESCRIPTION OF THE DRAWINGS

FIG. 1 is a front elevational view of the eyelid speculum device of the present invention and of an eye, showing how gripping portions of two elongated arms of the device may be squeezed together by a person's fingers in order to insert or position the device between the eyelids of the eye;

FIG. 2 is a view taken like FIG. 1, showing how the gripping portions of the arms may be released so that the arms engage the eyelids and hold the eyelids open;

FIG. 3 is a front elevation view of the eyelid speculum device of FIG. 1 before the gripping portions are squeezed together;

FIG. 4 is a top plan view of the eyelid speculum device of FIG. 3; and

FIG. 5 is a perspective view of the eyelid speculum device of FIG. 3.

DESCRIPTION OF THE PREFERRED EMBODIMENT

The following specification taken in conjunction with the drawings sets forth the preferred embodiment of the present invention in such a manner that any person skilled in the art can make and use the invention. The embodiment of the invention disclosed herein is the best mode contemplated by the inventors for carrying out their invention in a commercial environment, although it should be understood that various modifications can be accomplished within the parameters of the present invention.

FIGS. 1 through 5 show an eyelid speculum device 10 of the present invention used to hold a person's upper and lower eyelids 12 open to allow access to an eye or eyeball 14 for examination, treatment, ocular surgery, or some other reason. The speculum device 10 has two elongated arms 16, each arm 16 having one end 18 thereof as a free end, and the other end 20 thereof attached to a joining member 22.

Gripping portions 24 are attached to or integrally formed as part of the arms 16. The gripping portions 24 are generally L-shaped when viewed as in FIG. 3, and may be grasped by a person's fingers 26 and forced or squeezed together as illustrated in FIG. 1, so that curved portions 28 of the gripping portions 24 touch or contact each other. The arms 16 have reinforcing portions 30 adjacent ends 20 which increase the cross-sectional area or the structural rigidity of the arms 16 near number 22. As a result, the arms 16 return to their original positions or the device 10 returns to its original configuration shown in FIG. 3 when the gripping portions 24 are released. As best seen in FIG. 4, the cross-sectional area of the elongated arms 16 is reduced between portions 24 and 30. This facilitates bending of the arms 16.

The arms 16 are preferably made out of lightweight, durable, polyester material, or the like, which may be sterilized and is non-magnetic and anti-reflective. However, any other suitable material may be used, which is resilient and has a modulus of elasticity that allows bending of the arms 16 without permanent deformation thereof, and causes the arms 16 to return to their original positions as shown in FIG. 3 after the gripping portions 24 are released. Alternatively, a spring (not shown) may be used to bias the arms 16 apart. Such a spring may be located, for example, in member 22. The device 10 may be injection molded, or may be manufactured using any desirable method of fabrication.

As shown in FIG. 5, each arm 16 has a concave surface 34 extending along the length thereof. Surface 34 facilitates engaging the upper and lower eyelids 12.

Referring again to FIG. 3, the elongated arms 16 are curved, when viewed from the front of the device 10, and the eyelid speculum device 10 generally conforms to the shape of a person's eye, or to the length and/or curvature of the eyelids 12. This facilitates placing the device 10 between the upper and lower eyelids 12, and engaging the arms 16 to the eyelids 12. Also, as shown in FIG. 3, the ends 18 and 20 of the arms 16 curve backward, as indicated by curvature 32, when viewed from the top of the device 10. This curvature 32 generally conforms to the curvature of the eyelids 12, and facilitates engagement of the arms 16 to the eyelids 12.

The eyelid speculum device 10 is used by a person first grasping gripping portions 24 with his or her fingers 26, and squeezing the portions 24 together, which causes the arms 16 to bend until curved portions 28 contact each other. The device 10 is then inserted between the upper and lower eyelids 12 of a person's eye 14 so that joining member 22 is located adjacent to the person's nose. The gripping portions 24 are then released causing the elongated arms 16 to move away from each other, or to move toward their original positions. As the arms 16 separate, edges 44 of the arms 16 (see FIG. 5) slip under the upper and lower eyelids 12, and concave surfaces 34 engage the eyelids 12. As engagement occurs, biasing forces apply pressure to the eyelids 12.

As discussed above, the elongated arms 16 are curved to generally conform to the curvature and/or length of the upper and lower eyelids 12. Therefore, a substantial length of the elongated arms 16 engages the eyelids 12, resulting in reduced pressure or reduced biasing forces being applied to the eyelids 12, or a more uniform pressure being applied to the eyelids 12 along the length of the arms 16. As such, the speculum device 10 decreases the chance that post-operative ptosis or drooping of the eyelids 12 will occur. By "a substantial length" is meant a length having a range of from about one half of the length of the arm 16 to about the length of the arm 16.

The speculum device 10 will be securely held in place due to engagement of the upper and lower eyelids over a substantial length of the elongated arms 16. As a result, adhesive tape or other supporting devices are not needed to hold the device 10 in place between the upper and lower eyelids.

Eyelid speculum devices 10 of different dimensions may be used to satisfy the needs of different patients. For example, a smaller size device 10 may be needed for a child. Referring again to FIG. 3, one preferred embodiment of the device 10 has an overall length 36 of about 3.20 cm, length 40 of about 2.80 cm, height 38 of about 1.75 cm. However, any desirable dimensions may be used for the device 10.

The device 10 may be used for other applications. For example, the device 10 may be used to hold an incision open, or for other purposes. The present invention may be used for any desirable purpose other than as an eyelid speculum device.

The above description discloses the preferred embodiment of the present invention. However, persons of ordinary skill in the art are capable of numerous modifications once taught these principles. Accordingly, it will be understood by those skilled in the art that changes in the form and details may be made to the above-described embodiments without departing from the spirit and scope of the invention.

We claim:

1. An eyelid speculum device for retracting a patient's eyelids, comprising:
  a pair of elongated arms each having first and second ends, said first ends being joined together, said second ends defining arm free ends;
  wherein said arms, when said free ends are squeezed together, are adapted to be inserted between a patient's eyelids;
  wherein said arms along substantial lengths thereof are oppositely concave shaped, the oppositely concave pair of arms lying generally in plane so as to conform to the curvatures of the respective eyelids; and
  wherein said arms are spring biased and configured to open up and directly engage, along their concave substantial arm lengths, the eyelids continuously along substantial lengths thereof, after said squeezed-together free ends are released, to thereby hold the eyelids open.

2. The eyelid speculum device of claim 1 wherein said first ends are directly joined together.

3. The eyelid speculum device of claim 1 further comprising gripping portions integrally formed at said free ends.

4. The eyelid speculum device of claim 3 wherein said gripping portions are oppositely and outwardly curved to provide manual squeezing engagement surfaces.

5. The eyelid speculum device of claim 1 wherein said arms are made of non-magnetic polyester.

6. The eyelid speculum device of claim 1 wherein said arms are made by injection molding.

7. The eyelid speculum device of claim 1 wherein one of said oppositely concave shaped arms has an upper concave surface extending along the length thereof such that the concavity of said upper surface is substantially perpendicular to said plane in which said arms generally lie, thereby facilitating engagement of said one arm with the patient's upper eyelid, and wherein the other of said oppositely concave shaped arms has a lower concave surface extending along the length thereof such that the concavity of said lower surface is substantially perpendicular to said plane in which said arms generally lie, thereby facilitating engagement of said other arm with the patient's lower eyelid.

8. An eyelid speculum device for retracting eyelids, comprising:
- two elongated arms joined together at first ends thereof, and having free ends at second ends thereof;
- wherein said arms are adapted so that said device may be inserted between eyelids of a patient when said free ends are squeezed together;
- wherein said arms are adapted to engage the eyelids after said free ends are released;
- wherein each of said arms is contoured to generally conform to a different one of the eyelids;
- wherein a substantial length of each of said arms may engage a respective eyelid, said substantial length having a range of from about one half of the length of each said arm to about the full length of each said arm; and
- wherein one said arm defines a device upper arm having a concave surface extending along the upper length thereof facilitating engagement with the patient's upper eyelid, and the other said arm defines a device lower arm having a concave surface extending along the lower length thereof facilitating engagement with the patient's lower eyelid.

9. The eyelid speculum device of claim 8 wherein each of said arms has a continuous smooth curvature between said first and second ends thereof.

10. The eyelid speculum device of claim 8 wherein said first ends are joined together generally at a point.

11. An eyelid speculum device for retracting eyelids, comprising:
- two elongated arms joined together at first ends thereof, and having free ends at second ends thereof;
- wherein each of said arms is contoured to generally conform to a respective one of a patient's eyelids in one of his or her eyes;
- wherein said arms are adapted so that said device may be inserted between the eyelids when said free ends are squeezed together;
- wherein said arms are adapted to engage the eyelids after said free ends are released, and thereby apply biasing forces to the eyelids;
- gripping portions integrally formed at said free ends;
- a joining member attached to said first ends; and
- reinforcing portions integrally formed at said first ends;
- wherein one said arm defines a device upper arm having a concave surface extending along the upper length thereof facilitating engagement with the patient's upper eyelid, and the other said arm defines a device lower arm having a concave surface extending along the lower length thereof facilitating engagement with the patient's lower eyelid.

12. The eyelid speculum device of claim 11 wherein each of said arms defines along substantial lengths thereof an arc and said arcs intersect at said joining member.

13. An eyelid speculum device for retracting eyelids, comprising:
- two elongated arms joined together at first ends thereof, and having free ends at second ends thereof;
- wherein each of said arms is contoured to generally conform to a respective one of a patient's eyelids;
- wherein said arms are adapted so that said arms may be inserted between the eyelids when said free ends are squeezed together;
- wherein said arms are adapted to engage the eyelids after said free ends are released to hold the eyelids open; and
- wherein each said arm is resilient and has an eyelid-engageable, outwardly-disposed concave surface along substantial lengths thereof.

14. The eyelid speculum device of claim 13 further comprising gripping portions integrally formed at said free ends.

15. The eyelid speculum device of claim 14 further comprising a joining member attached to said first ends.

16. The eyelid speculum device of claim 15 further comprising reinforcing portions integrally formed at said first ends.

* * * * *